United States Patent [19]

Ebel et al.

[11] Patent Number: 4,668,785

[45] Date of Patent: May 26, 1987

[54] PREPARATION OF (2-HYDROXYETHYL)-MELAMINES AND THEIR USE AS MODIFIERS IN THE PREPARATION OF AMINOPLAST RESINS

[75] Inventors: Klaus Ebel, Ludwigshafen; Wolfgang Reuther, Heidelberg; Wolfram Weiss, Mutterstadt; Ludwig Lelgemann, Ludwigshafen, all of Fed. Rep. of Germany

[73] Assignee: BASF Aktiengesellschaft, Fed. Rep. of Germany

[21] Appl. No.: 744,203

[22] Filed: Jun. 13, 1985

[30] Foreign Application Priority Data

Jun. 15, 1984 [DE] Fed. Rep. of Germany ....... 3422218

[51] Int. Cl.$^4$ ............................................. C07D 251/70
[52] U.S. Cl. ..................................... 544/196; 544/205; 528/254; 528/258; 428/526; 428/528
[58] Field of Search ................ 544/205, 196; 528/254, 528/258

[56] References Cited

U.S. PATENT DOCUMENTS

| | | | |
|---|---|---|---|
| 2,328,961 | 9/1943 | D'Alelio | 544/197 |
| 2,393,755 | 1/1946 | D'Alelio | 544/197 |
| 2,467,523 | 4/1949 | Dudley | 210/24 |
| 2,723,244 | 11/1955 | Joyce | 528/423 |
| 3,244,713 | 4/1966 | Dowbenko | 544/205 |
| 4,312,988 | 1/1982 | Jacobs, III et al. | 544/196 |
| 4,369,286 | 1/1983 | Czepel et al. | 528/254 X |
| 4,424,261 | 1/1984 | Keeling et al. | 525/515 X |
| 4,448,849 | 5/1984 | Keeling et al. | 525/515 X |
| 4,591,613 | 5/1986 | Karam et al. | 528/254 X |
| 4,618,676 | 10/1986 | Ebel et al. | 544/196 |

FOREIGN PATENT DOCUMENTS 0106049 4/1984 European Pat. Off. .

*Primary Examiner*—Howard E. Schain
*Attorney, Agent, or Firm*—Keil & Weinkauf

[57] ABSTRACT

N,N',N"-tris-(2-hydroxyethyl)-melamine, if required, as a mixture with N-mono- and N,N'-bis-(2-hydroxyethyl)-melamine, is prepared by reacting melamine with ethanolamine in the presence of an acidic catalyst by a method in which the reaction is carried out at from 120° to 250° C. using an excess of ethanolamine, and the molar ratio of free ethanolamine to the sum of free and converted melamine is not permitted to fall below 4:1 during the entire reaction time, and the stated (2-hydroxyethyl)-melamines are used as modifiers in the prepartion of aminoplast resins which are suitable for laminating surfaces.

5 Claims, No Drawings

PREPARATION OF (2-HYDROXYETHYL)-MELAMINES AND THEIR USE AS MODIFIERS IN THE PREPARATION OF AMINOPLAST RESINS

The present invention relates to a novel process for the preparation of N,N',N''-tris-(2-hydroxyethyl)-melamine, optionally as a mixture with N-mono- and N,N'-bis-(2-hydroxyethyl)-melamine, by reacting melamine with an excess of ethanolamine, and to a process of using these (2-hydroxyethyl)-melamines as modifiers in the preparation of aminoplast resins which are suitable for laminating surfaces.

It has been disclosed that the amino groups of melamine can be exchanged for a variety of amines, such as alkylamines, arylamines or polyamines (U.S. Pat. Nos. 2,328,961, 2,393,755, 2,467,523 and 2,723,244).

Exchange for alkanolamines, eg. ethanolamine or isopropanolamine, has also been investigated.

For example, U.S. Pat. No. 3,244,713 describes the reaction of melamine with ethanolamine, these reactants being employed in the reaction in a molar ratio of 5:1. However, we have found that, under the reaction conditions stated there, only unsatisfactory yields of N,N',N''-tris-(2-hydroxyethyl)-melamine are obtained and at the same time large amounts of by-products are formed.

U.S. Pat. No. 4,312,988 discloses that, when malamine is reacted with ethanolamine, isomelamines are formed in a competing reaction with elimination of water, these isomelamines being responsible for the low yield of N,N',N''-tris-(2-hydroxyethyl)-melamine. For example, in the reaction of ethanolamine with melamine in a molar ratio of 3.2:1, the amount of isomelamines formed is 20% at 82% conversion, as high as 50% at 95% conversion, and finally 100% at 99% conversion.

It has therefore been suggested that isopropanolamine be used instead of ethanolamine. According to U.S. Pat. No. 4,312,988, formation of isomelamine can in fact only be reduced drastically if the straight-chain ethanolamine is replaced with a branched isoalkanolamine.

It is an object of the present invention to provide a novel process for the preparation of 2-(hydroxyethyl)-melamine which starts from melamine and ethanolamine and in which isomelamine formation is prevented.

We have found that this object is achieved, and that, contrary to existing opinon, N,N',N''-tris-(2-hydroxyethyl)-melamine, if required, as a mixture with N-mono- and N,N'-bis-(2-hydroxyethyl)-melamine, can advantageously be prepared by reacting melamine with ethanolamine in the presence of an acidic catalyst, if the reaction is carried out at from 120° to 250° C. using an excess of ethanolamine, and the molar ratio of free ethanolamine to the sum of free and converted melamine is not permitted to fall below 4:1 during the entire reaction time.

N,N',N''-tris-(2-hydroxyethyl)-melamine, N,N'-bis-(2-hydroxyethyl)-melamine and N'-mono-(2-hydroxyethyl)-melamine are of the general formula I

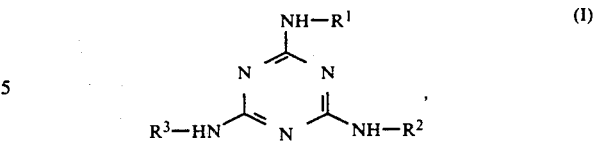

where $R^1$, $R^2$ and $R^3$ are each $-C_2H_4-OH$ in the case of N,N',N''-tris-(2-hydroxyethyl)-melamine, $R^1$ and $R^2$ are each $-C_2H_4-OH$ and $R^3$ is H in the case of N,N'-bis-(2-hydroxyethyl)-melamine, and $R^1$ is $C_2H_4OH$ and $R^2$ and $R^3$ are each H in the case of N-mono-(2-hydroxyethyl)-melamine.

The novel process gives virtually isomelamine-free N,N',N''-tris-(2-hydroxyethyl)-melamine, if desired, as a mixture with the corresponding mono and bis compounds. This ensures that the full NH and OH functionalities of these products are retained.

The process according to the invention is advantageously carried out by initially taking a mixture of melamine, ethanolamine, an acidic catalyst and, if required, a solvent, and heating the stirred mixture at 120°-250° C., in particular 150°-180° C.

The procedure is generally carried out under atmospheric pressure, but in order to reach the upper temperature range (from 180° to 250° C.), a pressure of from 1 to 15 bar has to be maintained.

It is also adjustable to carry out the reaction in the presence of a protective gas, the latter generally being passed over the surface of the reaction mixture. Examples of suitable protective gases are noble gases and in particular nitrogen.

Suitable acidic catalysts are all strong and moderately strong acids, eg. hydrofluoric acid, hydrochloric acid, hydrobromic acid, sulfuric acid, nitric acid, phosphoric acid, amidosulfonic acid, thiocyanic acid, p-toluenesulfonic acid or methanesulfonic acid.

The acids can be added either in the free form or as a melamine or ethanolamine salt, but may furthermore be added in the form of a salt of a base which is weaker than ethanolamine, for example in the form of an ammonium salt.

Apart from the stated protic acids, Lewis acids, such as boron trifluoride, aluminum chloride, tin(IV) chloride, antimony(V) fluoride or iron(III) bromide, also catalyze the reaction.

From 0.05 to 3 moles, preferably from 0.1 to 1 mole, of catalyst are employed per mole of melamine. Where the protic acid is used in the form of its melamine salt, the amount of melamine from the salt must be taken into account. The molar ratio of free ethanolamine to the sum of free and converted melamine must not fall below the required value of 4:1. The reaction rate is found to increase as the amount of catalyst is increased.

The novel process is preferably carried out in the absence of a solvent, although an organic solvent may also be used. Suitable solvents for this purpose are polyols, eg. ethylene glycol, 1,2-propylene glycol, diethylene glycol or triethylene glycol.

A critical parameter of the process is the molar ratio of free ethanolamine to the sum of free and converted melamine; this ratio must not fall below 4:1 during the entire reaction time. Converted melamine is considered to be the sum of N-mono-, N,N'-bis- and N,N',N''-tris-(2-hydroxyethyl)-melamine present in each case.

In a preferred embodiment of the novel process, the molar ratio of free ethanolamine to the sum of free and converted melamine is not permitted to fall below 6:1 during the entire reaction time.

From 6 to 15, preferably from 6 to 10, moles of ethanolamine are employed per mole of melamine.

Since increasing the amount of excess ethanolamine also results in a drop in the reaction rate, it is advisable, where it is desired to avoid fairly long reaction times, to begin the reaction using a small excess of ethanolamine and to add further ethanolamine in the course of the reaction.

The initial amount of ethanolamine is from 6 to 9, in particular 6, moles, per mole of melamine. The amount of ethanolamine added in the course of the reaction is as high as 9, preferably as high as 4, moles, per mole of melamine. The addition can be effected continuously or batchwise over a period of from 1 to 10 hours, but it is also possible to add the particular amount of the ethanolamine all at once.

The course of the reaction can be monitored by analytical methods, for example by means of high pressure liquid chromatography (HPLC). The reaction can be stopped at any degree of conversion, the resulting mixture of N,N',N''-tris-(2-hydroxyethyl)-melamine, N,N'-bis-(2-hydroxyethyl)-melamine and N-mono-(2-hydroxyethyl)-melamine having a defined, reproducible composition.

To isolate the desired products, the particular catalytic acid is neutralized by adding a base, eg. sodium hydroxide, potassium hydroxide, sodium carbonate, potassium carbonate, calcium carbonate or barium carbonate, in the solid state to the reaction mixture and separating off the precipitated salts.

Excess free ethanolamine is then distilled off under reduced pressure (about 30 mbar) and at about 180° C., the virtually colorless residue solidifying to a resin, which can easily be comminuted.

If the reaction is carried out to complete conversion (100%), pure, crystalline N,N',N''-tris-(2-hydroxyethyl)-melamine can be prepared.

Working up is carried out, as described above, likewise by neutralization, but in this case the precipitated salts are not isolated immediately but the excess ethanolamine is first distilled off directly. The residue is then taken up in butanol, the inorganic salt is separated off and methylene chloride is added to the butanolic solution. On cooling the mixture, N,N',N''-tris-(2-hydroxyethyl)-melamine is precipitated in the form of colorless crystals and is filtered off under suction.

The stated (2-hydroxyethyl)-melamines are very useful as modifiers in the preparation of aminoplast resins which are suitable for laminating surfaces (impregnating resins).

In general, aminoplast resins are resin-like products and their solutions, which are formed by precondensation of amino-containing or imino-containing compounds, ie. aminoplast formers, with carbonyl compounds, with or without alkanols, and which, under the action of high temperatures and/or acidic catalysts, can undergo further condensation with crosslinking to give macromolecules.

Important fields of use of the aminoplasts, in particular the melamine resins, are in the production of laminates and for laminating the surfaces of board materials. In this procedure, a decorative or protective layer is applied onto a base, which in turn consists of plastic or, preferably, of a woodworking material (fiberboard or particle board), by impregnating patterned or single-color paper or fabric webs with suitable aminoplast resins and laminating them under pressure, at a particular residual moisture content, with the boards of the material. The pressure during pressing can be from 1 to 25 N/mm$^2$, and the temperature from 120° to 200° C. During the pressing procedure, the aminoplast resin undergoes thermal curing, forms a protective layer and bonds the paper or fabric web to the board of the material. The laminated woodworking materials and laminates exhibit good chemical and physical stability.

The aminoplasts used to date for impregnating the paper or fabric webs intended for decorative or protective layers possess poor resilience in the cured state, and surfaces produced using these resins therefore tend to crack.

There has been no lack of attempts to overcome or reduce the problem of insufficient resilience of the decorative layer by using additives in the impregnating resins. In particular, ε-caprolactam, polyhydric alcohols, such as sorbitol and sugars, and aromatic sulfonamides have been recommended as modifiers of this type. However, when such additives are introduced, adequate resilience is achieved at the expense of insufficient water resistance of the cured resins.

We have found that N,N',N''-tris-(2-hydroxyethyl)-melamines prepared by the novel process, if necessary as a mixture with N-mono- and N,N'-bis-(2-hydroxyethyl)-melamine, can advantageously be used as modifiers in the preparation of aminoplast resins which are suitable for laminating surfaces.

The (2-hydroxyethyl)-melamines used according to the invention, preferably N,N',N''-tris-(2-hydroxyethyl)-melamine, are added to the aminoplasts advantageously in an amount of not more than 15, preferably from 0.5 to 15, in particular from 5 to 10, % by weight, based on the solids content of the aminoplast. While smaller amounts merely have correspondingly smaller effects, larger amounts may gradually alter the nature of the aminoplast resin itself. Moreover, in the case of larger amounts, it may sometimes be necessary also to add formaldehyde in order to effect curing.

Examples of suitable aminoplast formers are urea, thiourea, dicyanodiamide, guanamines, such as acetoguanamine or benzoguanamine, but in particular melamine, and examples of suitable carbonyl compounds are acetaldehyde, aromatic aldehydes and ketones, but in particular formaldehyde. Mixtures of these aminoplast formers and/or the stated carbonyl compounds may also be used for the preparation of the aminoplast.

Melamine/formaldehyde condensates and their co-condensates or mixtures with other aminoplast formers and formaldehyde, and their etherification products with short-chain alkanols, have proven particularly useful for the preparation of such resins. Melamine/formaldehyde condensates which contain from 60 to 100 mol% of melamine as an aminoplast former and from 60 to 100 mol% of formaldehyde as a carbonyl compound are preferably used. This means that a further 0–40 mol% of other aminoplast formers or carbonyl compounds can be present in each case.

The molar ratio of carbonyl compounds to aminoplast formers is in general from 1.4:1 to 2.2:1, in particular from 1.4:1 to 2:1, for the example of formaldehyde and melamine. If other aminoplast formers are used instead of, or together with, melamine, the molar ratio may change slightly, according to the known rules.

The modified aminoplasts are obtained if an aminoplast former is condensed with a carbonyl compound and, if required, with conventional modifiers in a known manner in aqueous solution, and the N,N',N''-tris-(2-hydroxyethyl)-melamine prepared by the novel process, if required, as a mixture with the mono and bis compounds, is added in the above amount, before, during or after the condensation, preferably before or during the condensation.

It is also possible for hydrolyzable salts of weak to strong carboxylic acids, sulfonic acids or mineral acids, eg. diethanolamine acetate, ethanolamine hydrochloride, ethylenediamine acetate, ammonium thiocyanate, ammonium lactate or ethylenediamine phosphate, to be added to the aminoplasts in order to accelerate curing, without the resilience of the coatings being adversely affected as a result.

In the preparation of the resins, other modifiers, such as monohydric or polyhydric alcohols, sugars, acid amides, such as dimethylformamide or $\epsilon$-caprolactam, salts of amidosulfonic acid and aromatic sulfonamides, may also be added. The agents may complement one another or partially replace one another. As a rule, condensation of the resins is continued until a finite water-dilutability is reached. In some cases, for example when fairly large amounts of salts of amidosulfonic acid are added, the resins obtained may also exhibit infinite water-solubility.

Semi-finished products for the production of decorative laminates or decorative laminated boards of woodworking materials are prepared by a method in which paper or fabric webs are impregnated, at least in the top layer, with the aminoplast solution, and dried at from 110° to 160° C. to a particular residual moisture content. For the production of laminates, the impregnated papers or fabric webs are pressed under elevated pressure and temperature together with, as a base, a plurality of layers of kraft papers impregnated with phenol resin. Pressing is carried out at about 120°–160° C. and under from 8 to 12 N/mm²; the pressing time depends on the thickness and, in the case of multiplaten presses, on the amount of laminates produced per platen, and can be, for example, from 10 to 80 minutes. Before the laminate is removed, it is advantageously recooled to about 60° to 70° C.

To produce laminated woodworking materials, the impregnated paper or fabric webs are pressed onto the prepared woodworking board under a pressure of, in general, from 1.5 to 2.5 N/mm² and at from 120° to 200° C.

Aminoplasts which contain the novel modifier are particularly useful for the production of laminates and laminated woodworking materials. We have in fact found that crack formation in the surface of laminates and woodworking materials can be eliminated, or the resilience of the surface substantially increased, if the paper or fabric web intended for the decorative or protective layer is impregnated with an aminoplast modified according to the invention, and then laminated with the woodworking board or converted to a laminate in a conventional manner.

The stated (2-hydroxyethyl)-melamines are also useful intermediates, for example for the synthesis of urethanes.

The Examples which follow illustrate the invention.

(A) Preparation

EXAMPLES 1 TO 5

Examples 1 to 5 were carried out under the same reaction conditions, the only difference being the amount of excess ethanolamine.

Example 1 is a comparative example and was carried out similarly to Example 7 of U.S. Pat. No. 3,244,713. As described there, the hydrochloric acid used as a catalyst was employed in the form of melamine hydrochloride.

In Examples 2 to 5, the catalyst used in each case was ammonium chloride.

Procedure for Examples 1 to 5:

Melamine, the catalyst and ethanolamine were stirred under reflux in an oil bath at 200° C., while a gentle stream of nitrogen was passed over the mixture. The reaction was monitored by taking samples hourly and subjecting them to HPLC and titration.

The weights of the samples and the evaluation of the HPLC results are shown in the Table below.

TABLE

| | Example 1 | | Example 2 | | Example 3 | | Example 4 | | Example 5 | |
|---|---|---|---|---|---|---|---|---|---|---|
| | Weight of sample (g) | Molar ratio | Weight of sample (g) | Molar ratio | Weight of sample (g) | Molar ratio | Weight of sample (g) | Molar ratio | Weight of sample (g) | Molar ratio |
| Melamine hydrochloride | 48.4 | 1 | — | — | — | — | — | — | — | — |
| Melamine | — | — | 42.0 | 1 | 42.0 | 1 | 31.5 | 1 | 31.5 | 1 |
| Ethanolamine | 91.5 | 5 | 122.0 | 6 | 163.0 | 8 | 153.0 | 10 | 228.8 | 15 |
| Ammonium chloride | — | — | 17.8 | 1 | 17.8 | 1 | 13.4 | 1 | 13.4 | 1 |
| | HPLC evaluation (% area) | | HPLC evaluation (% area) | | HPLC evaluation (% area) | | HPLC evaluation (% area) | | HPLC evaluation (% area) | |
| (A) Tris-HEM* | 44 | | 42 | | 42 | | 37 | | 52 | |
| By-products | 22 | | 9 | | 3 | | 2 | | 0.3 | |
| (B) Bis-HEM** | 4 | | 2 | | 4 | | 2 | | 2 | |
| Tris-HEM | 52 | | 60 | | 80 | | 91 | | 96 | |
| By-products | 41 | | 38 | | 16 | | 7 | | 2 | |

*Tris-HEM = N,N',N''—tris-(2-hydroxyethyl)-melamine
**Bis-HEM = N,N'—bis-(2-hydroxyethyl)-melamine In order to be able to compare the Examples, the concentration of by-products for about the same amount of tris substitution product (tris-HEM) of about 40% by area is listed under A) in each case.

The amounts of by-products for as large an amount of tris-HEM as possible are compared under B).

EXAMPLE 6

160 g (1.6 moles) of sulfuric acid were added dropwise to a stirred mixture of 1,008 g (8.0 moles) of melamine and 3,910 g (64.0 moles) of ethanolamine, after which the heterogenous reaction mass was stirred under reflux while a gentle stream of nitrogen was passed over the mixture. After a reaction time of from 25 to 28 hours, an HPLC determination showed that the solution, which was then clear and colorless, had a triazine composition of about 11 mol% of mono-(2-hydroxyethyl)-melamine, 49 mol% of bis-(2-hydroxyethyl)-melamine and 40 mol% of tris-(2-hydroxyethyl)-melamine, with less than 2% of isomelamines, the percentages being based on the hydroxyethylmelamines. The mixture was worked up by neutralizing it by adding 128 g (3.2 moles) of solid sodium hydroxide at 100° C., and filtering the hot solution under suction through a G4 frit. The filtrate was freed from excess ethanolamine at 180° C. and under 30 mbar. The residue from distillation solidified on cooling to give a virtually colorless resin-like mass (1,650 g) which consisted of about 11 mol% of mono-(2-hydroxyethyl)-melamine, 49 mol% of bis-(2-hydroxyethyl)-melamine and 40 mol% of tris-(2-hydroxyethyl)melamine and could readily be comminuted. The product also contained 3% of ethanolamine, 0.2% of sodium sulfate and not more than 3% of isomelamine.

EXAMPLE 7

504 g (4 moles) of melamine, 2,440 g (40 moles) of ethanolamine and 214 g (4 moles) of ammonium chloride were refluxed for 27 hours, as described in Example 6. Thereafter, the mixture was neutralized by adding 160 g (4 moles) of solid sodium hydroxide at 100° C. and the excess ethanolamine was distilled off at from 150° to 190° C. and under 30 mbar. The virtually colorless residue was dissolved in 1,000 ml of n-butanol with heating, the precipitated sodium chloride was filtered off hot under suction, and 300 ml of methylene chloride were added to the filtrate at from 30° to 40° C. When the mixture was cooled, the pure product crystallized out and was filtered off under suction and dried. 846 g (81%) of N,N',N''-tris-(2-hydroxyethyl)-melamine of melting point 95° C. were obtained.

(B) Use

EXAMPLES 8 TO 10

Decorative paper having a basis weight of 80 g/m² was impregnated with an aqueous melamine/formaldehyde resin solution (solids content 55% by weight) and dried for 5 minutes at 160° C. The amount of resin applied was about 120% by weight, based on the weight of base paper, and the residual moisture content was about 6.5% by weight, based on the treated paper.

The melamine/formaldehyde resin used had a molar ratio of melamine or formaldehyde of 1:1.7 and was brought to a turbidity point of 4.5 minutes at 100° C. with an acidic curing agent.

The impregnated papers were pressed onto 16 mm thick particle boards under 2 N/mm², under the following conditions:
(a) 50 seconds at 190° C., without recooling
(b) 100 seconds at 160° C., without recooling
(c) 360 seconds at 140° C., followed by recooling to 50° C. under pressure.

Pressing was carried out using liner pads. The stated temperatures refer to the temperature of the press.

The test results are summarized in the Table below.

|  | Example 8 (Comparison) | Example 9 (Comparison) | Example 10 |
| --- | --- | --- | --- |
| Modifier | — | Butane-1,4-diol | N,N',N''—tris-(2-hydroxyethyl)-melamine |
| Amount, based on resin solution [% by weight] | — | 6 | 6 |
| Gloss [refractometer units] | (a) 60 (b) 70 (c) 90 | (a) 25 (b) 30 (c) 70 | (a) 40 (b) 50 (c) 80 |
| Change in gloss (after exposure to steam for 1 hour)* |  |  |  |
| before | 90 | 70 | 80 |
| after [refractometer units] | 85 | 35 | 70 |
| Cracking (24 hours at 80° C.)** | pronounced | none | none |

*cf. DIN 53,799
**cf. DIN 68,765 and DIN 53,799

We claim:
1. A process for the preparation of N,N',N''-tris-(2-hydroxyethyl)-melamine, by reacting melamine with ethanolamine in the presence of an acidic catalyst, wherein the reaction is carried out at from 120° to 250° C. using an excess of ethanolamine, and the molar ratio of free ethanolamine to the sum of free and converted melamine is not permitted to fall below 4:1 during the entire reaction time.
2. The process of claim 1, wherein the reaction is carried out from 150° to 180° C. and under atmospheric pressure.
3. The process of claim 1, wherein the reaction is carried out in the absence of a solvent.
4. The process of claim 1, wherein from 6 to 15 moles of ethanolamine are used per mol of melamine.
5. The process of claim 1, wherein a mixture is prepared which contains N,N',N''-tris-(2-hydroxyethyl)-melamine and N-mono- and N,N'-bis-(2-hydroxyethyl)-melamine.

* * * * *